(12) United States Patent
Pardue et al.

(10) Patent No.: US 6,691,638 B2
(45) Date of Patent: Feb. 17, 2004

(54) METHODS FOR GAMETE PRODUCTION IN BIRDS

(75) Inventors: Samuel Pardue, Raleigh, NC (US); James Petitte, Raleigh, NC (US); Susan D'Costa, Raleigh, NC (US); Yonghong Song, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 10/074,719

(22) Filed: Feb. 12, 2002

(65) Prior Publication Data
US 2003/0111016 A1 Jun. 19, 2003

Related U.S. Application Data

(63) Continuation-in-part of application No. 09/533,141, filed on Mar. 23, 2000, now Pat. No. 6,354,242.

(51) Int. Cl.[7] .................. A01K 45/00; A61K 35/54
(52) U.S. Cl. ........................... 119/6.8; 424/582
(58) Field of Search ............... 119/6.8; 424/582

(56) References Cited

U.S. PATENT DOCUMENTS

| | | | |
|---|---|---|---|
| 5,162,215 A | 11/1992 | Bosselman et al. | 800/23 |
| 5,438,954 A | 8/1995 | Phelps et al. | 119/6.8 |
| 5,784,992 A | 7/1998 | Petitte et al. | 119/6.8 |
| 5,817,320 A | 10/1998 | Stone | 424/278.1 |
| 5,830,510 A | 11/1998 | Petitte et al. | 424/582 |
| 6,354,242 B1 | 3/2002 | Pardue et al. | 119/6.8 |

FOREIGN PATENT DOCUMENTS

| | | | | |
|---|---|---|---|---|
| WO | WO 93/14629 | 8/1993 | | A01K/67/04 |
| WO | WO 93/15185 | 8/1993 | | C12N/5/00 |
| WO | WO 01/70015 | 9/2001 | | A01K/45/00 |

OTHER PUBLICATIONS

Aige–Gil, "Sterilisation of avian embryos with busulphan," *Research in Veterinary Science* 50:139–144 (1991).

Andersson et al.; "Acute safety and pharmacokinetics of intravenous busulfan when used with oral busulfan and cyclophosphamide as pretransplantation conditioning therapy: a phase I study," *Biol Blood Marrow Transplant.* 6(5A): 548–54 (2000).

Bhagwatwar et al.; "Formulation and stability of busulfan for intravenous administration in high–dose chemotherapy," *Cancer Chemother Pharmacol* 37: 401–408 (1996).

Bishop et al.; "Toxicological review of busulfan (Myleran)," *Radiation Research* 168: 15–45 (1986).

Bresler et al.; "Manipulations of Germ–cell Populations in the Gonad of the Fowl," *British Poultry Science* 35:241–247 (1994).

Brunström; "A Method for Studying Embryotoxicity of Lipophilic Substances Experimentally Introduced Into Hens' Eggs," *AMBIO* 11(4): 209–211 (1982).

(List continued on next page.)

*Primary Examiner*—Yvonne Abbott

(57) ABSTRACT

The present invention provides methods for the production of avian gametes, comprising reducing endogenous primordial germ cells (PGCs) in a recipient bird in ovo and introducing donor primordial germ cells from another bird into the recipient bird in ovo. The present invention further provides a method of increasing the ratio of male offspring from a female bird, comprising reducing endogenous PGCs in the female bird in ovo, introducing donor PGCs from another bird into the female bird in ovo, and incubating the female bird to hatch. The female bird is raised to sexual maturity and bred to produce a plurality of eggs having a higher proportion of male eggs than in the absence of the inventive methods. In some embodiments, the donor PGCs are from a different species than the recipient bird. In preferred embodiments, endogenous PGCs are reduced using busulfan.

46 Claims, 1 Drawing Sheet

OTHER PUBLICATIONS

Bucci et al.; "Effects of busulfan on murine spermatogenesis: cytotoxicity, sterility, sperm abnormalities, and dominant lethal mutations," *Radiation Research* 176:259–268 (1987).

D'Costa et al.; "Production of interspecific embryonic germline chimeras by the intravascular transfer of gonadal PGCs," Transgenic Animal Meeting, Sep. 9–13, 2001, Reno, NV. Abstract.

D'Costa; "Characterization of turkey primordial germ cells and the production of interspecific embryonic chimeras," Dissertation submitted to North Carolina State University Department of Physiology (1999).

Hallett; "The Effects of Busulfan on Gonadal Differentiation and Development in Japanese Quail," *Poultry Science* 70:1619–1623 (1991).

Hemsworth et al.; "Effect of Busulphan on the Foetal Gonad," *Nature* 195:816–817 (1962).

Hirshfield, "Relationship between the Supply of Primordial Follicles and the Onset of Follicular Growth in Rats," *Biology of Reproduction* 50:421–428 (1994).

Kim et al.; "Development of a Positive Method for Male Stem Cell–Mediated Gene Transfer in Mouse and Pig," *Molecular Reproduction and Development* 46: 515–526 (1997).

Merchant–Larios et al.; "The effect of busulfan on rat primordial germ cells at the ultrastructural level," *Cell Differentiation* 8:145–155 (1979).

Pardue et al.; "Production of inter–and intra–specific germline chimeras in poultry," *Proceedings of the Australian Poultry Science Symposium*. 14, Feb. 11–13, 2002, Sydney, Australia.

Swartz, William J.; "Response of Early Chick Embryos to Busulfan," *Teratology* 21: 1–8 (1980).

Vick et al.; "Germ–line chimeras can produce both strains of fowl with high efficiency after partial sterilization," *Journal of Reproduction and Fertility* 98:637–641 (1993).

Wentworth et al.; "Manipulating of avian primordial germ cells and gonadal differentiation," *Poultry Science* 68(7):999–1010 (1989).

Westerhof et al.; "Comparison of different busulfan analogues for depletion of hematopoietic stem cells and promotion of donor–type chimerism in murine bone marrow transplant recipients," *Cancer Research* 60(19):5470–5478 (2000).

Chang et al.; "Production Of Germline Chimeric Chickens By Transfer Of Cultured Primordial Germ Cells," *Cell Biology International* 21:8, 495–499 (1997).

Kagami et al.; "Sexual Differentiation Of Chimeric Chickens Containing ZZ And ZW Cells In The Germline," *Molecular Reproductive Development*. 42, 379–387 (1995).

Kagami et al.; "The Developmental Origin Of Primordial Germ Cells And The Transmission Of The Donor–Derived Gametes In Mixed–Sex Germline Chimeras To The Offspring In The Chicken," *Molecular. Reproductive Development* 48, 501–510 (1997).

Kino et al.; "Production Of Chicken Chimeras From Injection Of Frozen–Thawed Blastodermal Cells," *Poultry Science*, 76, 753–760 (1997).

Mueller et al.; "Chimeric Pigs Following Blastocyst Injection Of Transgenic Porcine Primordial Germ Cells," *Mol. Reprod. Dev.* 54, 244–254 (1999).

Naito et al.; "Differentiation Of Donor Primordial Germ Cells Into Functional Gametes In The Gonads Of Mixed–Sex Germline Chimeric Chickens Produced By Transfer Of Primordial Germ Cells Isolated From Embryonic Blood," *Journal of Reproduction and Fertility* 117:2, 291–298 (1999).

Naito et al.; "Donor Primordial Germ Cell–Derived Offspring From Recipient Germline Chimaeric Chickens: Absence Of Long Term Immune Rejection And Effects On Sex Ratios," *British Poultry Science* 39, 20–23 (1998).

Naito et al.; "Preservation Of Chick Primordial Germ Cells In Liquid Nitrogen And Subsequent Production Of Viable Offspring," *Journal of Reproduction and Fertility* 102, 321–325 (1994).

Naito et al.; "Production Of Germline Chimeric Chickens, With High Transmission Rate Of Donor–Derived Gametes, Produced By Transfer Of Primordial Germ Cells," *Mol. Reprod. Dev.* 39, 153–161 (1994).

Ono et al.; "Transfer Of Male Or Female Primordial Germ Cells Of Quail Into Chick Embryonic Gonads," *Exp. Anim.* 45, 347–352 (1996).

Reynaud; "Capacites reproductrices et descendence de Poulet ayant submi un transfert de cellules germinales primordiales durant la vie embryonnaire," *Arch. Dev. Bio.* 179, 85–110 (1976).

Reynaud; "Transfert de cellules germinales primordiales de dindon a l'embryon de poulet par injection intravasculaire," *J. Embryol. Exp. Morphol* 21, 485–507 (1969).

Shaw et al.; "The Fate Of Female Donor Blastodermal Cells In Male Chimeric Chickens," *Biochem. Cell. Biol.* 70, 1218–1229 (1992).

Simkiss et al.; "Female Chromosomes In Cockerel Ejaculates," *Proc. R. Soc. Lond. B. Biol. Sci.* 263, 1245–1249 (1996).

Tagami et al.; "Developmental Origin Of Avian Primordial Germ Cells And Its Unique Differentiation In The Gonads Of Mixed–Sex Chimeras," *Mol. Reprod. Dev.* 50:3, 370–376 (1998).

Tagami et al.; "Differentiation Of Female Chicken Primordial Germ Cells Into Spermatozoa In Male Gonads," *Dev. Growth. Differ.* 39, 267–271 (1997).

Tajima et al., "Production Of Germ–Line Chimeras By Transfer Of Cryopreserved Gonadal Primordial Germ Cells (gPGCs) In Chicken," *J. Expt. Zool.* 280, 265–267 (1998).

Tajima et al.; "Production Of Germline Chimera By Transfer Of Primordial Germ Cells In The Domestic Chicken," *Theriogenology* 40, 509–519 (1993).

Thoraval et al.; "Somatic And Germline Chicken Chimeras Obtained From Brown And White Leghorns By Transfer Of Early Blastodermal Cells," *Poultry Science* 73, 1897–1905 (1994).

Yasuda et al.; "A Method To Obtain Avian Germ–Line Chimeras Using Isolated Primordial Germ Cells," *J. Reprod. Fertil.* 96, 521–528 (1992).

Pardue, Sam, Oral Presentation, "Production of Inter–and Intra–Specific Germ Line Chimeras in Poultry," *Australian Poultry Science Symposium* Feb. 12, 2002.

Petitte et al., "Production of somatic and germline chimeras in the chicken by transfer of early blastodermal cells," *Development* 108: 185–189 (1990).

Petitte et al., "Assessment of functional gametes in chickens after transfer of primordial germ cells," *J. Reprod. Fert.* 92: 255–229 (1991).

Vick et al., "Transgenic birds from transformed primordial germ cells," *Proc. R. Soc. Lond.*251: 179–182 (1993).

D'Costa et al., "Interspecific embryonic germline chimeras produced by the transfer of gonadal PGCs," *Poultry Science* 81(1): 107 (2002).

D'Costa et al., "Comparative Development of Avian Primordial Germ Cells and Production of Germ Line Chimeras," *Avian and Poultry Biology Reviews* 12(4): 151–168 (2001).

International Search Report, PCT/US01/09250 May 5, 2003.

METHODS FOR GAMETE PRODUCTION IN BIRDS

RELATED APPLICATION INFORMATION

This application is a continuation-in-part of U.S. application Ser. No. 09/533,141, filed Mar. 23, 2000 (allowed) now U.S. Pat. No. 6,354,242; the disclosure of which is incorporated by reference herein in its entirety.

FIELD OF THE INVENTION

The present invention concerns methods of transferring primordial germ cells to birds for the production of gametes therein. Such methods are useful in the conservation of endangered avian species, in reducing the time required to produce spermatozoa from slowly maturing species such as turkeys, decreasing the costs of maintaining breeder flocks, and altering the sex ratio of offspring flocks (e.g., to enhance the efficiency of production).

BACKGROUND OF THE INVENTION

The ability to more easily produce gametes of particular avian species would be extremely useful to the avian veterinary and poultry production fields. For endangered species such as the whooping crane, it would be extremely useful to have a ready supply of male spermatozoa. For commercial birds such as turkeys, it would be desirable to more quickly and economically produce male spermatozoa. For meat-producing flocks, it is desirable to have ways to increase the ratio of male birds in the flock. Accordingly, there is a need for new ways to obtain avian spermatozoa.

Chimeras are composite organisms consisting of cells derived from more than one zygote. Experimental chimeras have been used to study cell to cell interaction and cell lineage analysis during development (A. McLaren, *Mammalian Chimeras*. Cambridge University Press, Cambridge (1976)). When chimeras are produced using material derived from very early embryos, organisms develop containing a full mixture of somatic tissues. If the starting material includes early germ cells or their precursors, the resulting individuals will produce gametes of both the donor and recipient genotypes. In addition, chimeras can be intraspecific, i.e. between two zygotes of the same species, or interspecific, i.e. between two different species.

Avian primordial germ cells (PGCs) like other vertebrate germ cells are extragonadal in origin and must undergo a complex journey to reach the gonad. The transfer of blastodermal cells and primordial germ cells has produced avian germline chimeras. Reynaud (*J. Embryol. Exp. Morphol.* 21:485–507 (1969)), a pioneer in the production of avian germline chimeras, reported the production of turkey-chicken germline chimeras by the intravascular transfer of dissociated turkey germinal crescent cells into previously sterilized chick embryos (accomplished by exposure of the recipient germinal crescent to ultra-violet light). PGCs obtained by mechanical dissociation of the endoderm of the germinal crescent (stage 5) were injected into the blood vessels of chicken embryos (3–5 days of incubation). Prior to injection the recipient embryos were sterilized at stage 8–10 (H&H) with ultraviolet light; however, the sterilization was not complete and caused problems with development and mortality. The turkey PGCs in the chick embryo were identified solely on the basis of their nucleo-cytoplasmic ratio. This method of identification was difficult and tenuous and could not be used for actively dividing turkey PGCs since the dividing germ cells gave an aberrant nucleo-cytoplasmic ratio.

In a succeeding study, the transferred PGCs were allowed to undergo maturation in the host gonads and apparently could give rise to gametes but they were not suitable for fertilization (Wilhelm, *Roux's Arch. Dev. Bio.* 179:85–110 (1976)). The spermatozoa were incapable of fertilizing turkey eggs. They fertilized chick eggs but there was no normal development. Chicken spermatozoa were capable of activating the eggs obtained from female interspecific chimeras but they did not give rise to embryos. When the eggs were fertilized by turkey spermatozoa they developed into abnormal embryos that did not survive beyond stage 38 (H&H). Reynaud (*J. Embryol. Exp. Morphol.* 21:485–507 (1969)) used morphology as the only distinguishing characteristic in an attempt to identify turkey germ cells from chicken germ cells. Morphology alone is not sufficient for identifying chimeras and must be substantiated with other markers.

By reducing endogenous PGCs, the efficiency of generating germline chimeras, by repopulating the gonads with the desired donor PGCs, may be enhanced. A number of approaches to reduce PGCs have been utilized with varying degrees of success. Continuous exposure (20 days) to gamma irradiation (0.3–3.4 R/hr, $^{60}$Co) resulted in the complete destruction of oocytes at a dosage level of 3.4 and 1.8 R/hr (Mraz and Woody, *Radiation Research* 54:63–68 (1973)). However, hatchability was reduced at levels of 0.9 R/hr or higher. The application of continuous low-level gamma irradiation to reduce endogenous PGC is limited due to the relatively small numbers of eggs that can be exposed at any one time and the long period of exposure required.

Short-term exposure to a gamma source has also been attempted (Carsience et al., *Development* 117:669–75 (1993); Thoraval et al., *Poultry Sci.* 73:1897–1905 (1994); Maeda et al., *Poultry Science* 77:905–07 (1998)). In these studies, unincubated eggs were exposed to 500–700 rads just prior to the injection of stage X blastodermal or area pellucida cells. The incidence of germline chimerism following short-term gamma irradiation was highly variable. The basis for the inconsistent results were ascribed to "donor cells being injected into an inappropriate location . . . " (Carsience et al., *Development* 117:669–75 (1993)).

Attempts to sterilize recipient embryos using ultraviolet light have been described (Reynaud, *J. Embryol. Exp.Morphol.* 21:485–507 (1969); Reynaud, J., *Roux's Archives of Developmental Biology* 179:85–110 (1976); Aige-Gil and Simkiss (*Brit. Poul. Sci.* 32:427–438 (1991)). Aige-Gil and Simkiss concluded "it is not possible to irradiate the germinal crescent, particularly at stage 4 of incubation, without inducing major abnormalities". The level of sterility appeared to be positively correlated with developmental abnormalities, thus limiting the practical use of UV-light as a means to reduce endogenous PGC.

The compound busulfan (1,4-butanediol dimethane sulfonate, BU) has been used as a chemotherapeutic agent in the treatment of leukemia (Bhagwatwar et al., *Cancer, Chemotherapy & Pharmacology* 37:401–08 (1996)). In 1963, Hemsworth and Jackson demonstrated that the administration of BU in rats could markedly impair the development of PGCs (Hemsworth and Jackson, *J. Reproduction & Development* 6:229–33 (1963)). Injection of BU into the yolk sac of chick embryos resulted in multiple malformations (Swartz, *Teratology* 21:1–8 (1980)). Hallett and Wentworth (*Poultry Science* 70:1619–23 (1991)) also report significant declines in hatchability following injection of an albumen suspension of BU into quail eggs. In some BU treated quail, there appeared to be an absence of germ cells in the gonads, while other similarly treated birds appeared normal. The authors suggested that "inconsistencies in the delivery of BU to the embryo" might explain the observed variation. They concluded that discovering a non-toxic solvent system would be necessary to eliminate the inconsistent results associated with use of a suspension. Aige-Gil and Simkiss (*Brit. Poul. Sci.* 32:427–438 (1991)) used saline or sesame oil suspensions of BU, or solublized BU in dimethyl sulphoxide (DMSO) in chick embryos. Administration of DMSO alone produced embryonic mortality, developmental delays, and malformations that exceeded those observed with saline. The teratogenic effects were greatly minimized when BU was suspended in sesame oil and injected into yolk. Injection of 100 µg BU in sesame oil resulted in a sterility index of 95+%. In a subsequent experiment, Vick and co-workers (*J. Reproduction & Fertility* 98:637–41 (1993)) reported that the injection of 25, 50 and 250 µg BU significantly reduced gonadal germ cells in chick embryos. They estimated that BU treatment increased the rate of germline chimerism 3.5-fold when compared to non-BU treated embryos. Bresler et al. (*British Poultry Science* 35:241–47 (1994)) demonstrated that treatment with BU and subsequent injection of PGCs could result in a significant repopulation of the gonad. Injection of 50 µg BU, suspended in sesame oil reduced PGCs in the left and right gonad of 6 day-old chick embryos by 75 and 78%, respectively. Following the injection of a suspension of germinal crescent cells into BU-treated embryos, PGC numbers increased to 72 and 115% of controls for the left and right gonad, respectively.

The variability in delivery of BU to the gonad, and the resulting inconsistency in the effectiveness in reducing the number of PGCs, limits the usefulness of this technology.

Accordingly, there remains a need for new ways to accomplish the production and transfer of avian gametes.

SUMMARY OF THE INVENTION

A method for the production and collection of avian gametes comprises: reducing the number of primordial germs cells in a recipient avian subject in ovo; providing donor primordial germ cells from a donor avian subject; introducing the donor primordial germs cells into the recipient avian subject in ovo; incubating the recipient avian subject to hatch; and then raising the recipient avian subject to sexual maturity; wherein the recipient avian subject at sexual maturity produces gametes (e.g., sperm from male birds or ova from female birds) derived from the donor avian subject. In particular embodiments of the invention, the gametes are collected from the recipient avian subject. In other particular embodiments, the recipient avian subject is from a different species than the donor avian subject. For example, the donor avian species may be a whooping crane, and the recipient avian species may be a sand hill crane. In another example, the donor avian species may be a turkey, and the recipient avian species may be a chicken.

The production of turkey-chicken chimeras has wide applications. The transfer of male turkey PGCs is useful for turkey spermatogenesis in chicken gonads. This could accelerate spermatogenesis because the time required for production of sperm in chickens is 18 weeks as compared to 30 to 32 weeks in turkeys. The ability to culture PGCs and make germline chimeras could reduce the number of superior turkey sires currently needed to produce offspring. The ability to produce turkey sperm from a smaller and cheaper bird might also benefit the poultry industry.

The experimental chimeras could also provide a model to study the interaction between germ cells and somatic cells of different genotypes whereby it becomes possible to inquire whether its neighboring cells impose any of the germ cell characteristics upon it. This technique could also be utilized to transfer PGCs from low fecundity strains to more prolific birds, and for preserving PGCs in case of unexpected death or disease or in case an avian species is endangered under natural mating conditions (A. Tajima et al., *Theriogenology* 40:509–519 (1993)).

This aspect of the invention may also be practiced to increase the proportion of Z or W gametes produced by an avian subject. Typically, the inventive methods will be employed to increase the production of Z gametes (i.e., by the transfer of male, ZZ, PGCs). In birds, unlike mammals, it is the male that is the homogametic sex (ZZ) and the female which is the heterogametic sex (Zw). Therefore, in birds, it is the female that determines the gender of the offspring since she produces ova which carry either the Z or w chromosome. Thus, as noted below, by transferring male primordial germ cells (ZZ genotype) to female embryonic hosts, the percentage of Z-bearing ova produced by that host is increased and the percentage of male offspring is increased. An increase in the percentage of male offspring from broiler flocks is economically desirable for the corresponding greater feed conversion ratio and more efficient meat production so obtained.

Accordingly, a second aspect of the present invention is a method of increasing the proportion of male birds in a plurality of bird eggs, comprising: reducing the number of primordial germ cells in a female bird in ovo; introducing male (ZZ) avian primordial germ cells into the female bird in ovo; incubating the female bird to hatch; raising the female bird to sexual maturity; and then breeding the bird to produce a plurality of fertile bird eggs (with the ratio of male to female bird eggs produced from the bird being greater than that obtained in the absence of administering the male primordial germ cells to the bird in ovo). Typically, the method further comprises the step of incubating the plurality of bird eggs to hatch (with the ratio of male to female birds produced from the plurality of eggs being greater than that produced in the absence of administering the male primordial germ cells to the female bird in ovo). The female bird may be of any suitable species, such as chicken or turkey, and the primordial germ cells being administered are preferably from the same species as the female bird to which they are administered.

The foregoing and other objects and aspects of the present invention are explained in detail in the specification set forth below.

DETAILED DESCRIPTION OF THE PREFERRED EMBODIMENTS

Figure 1:
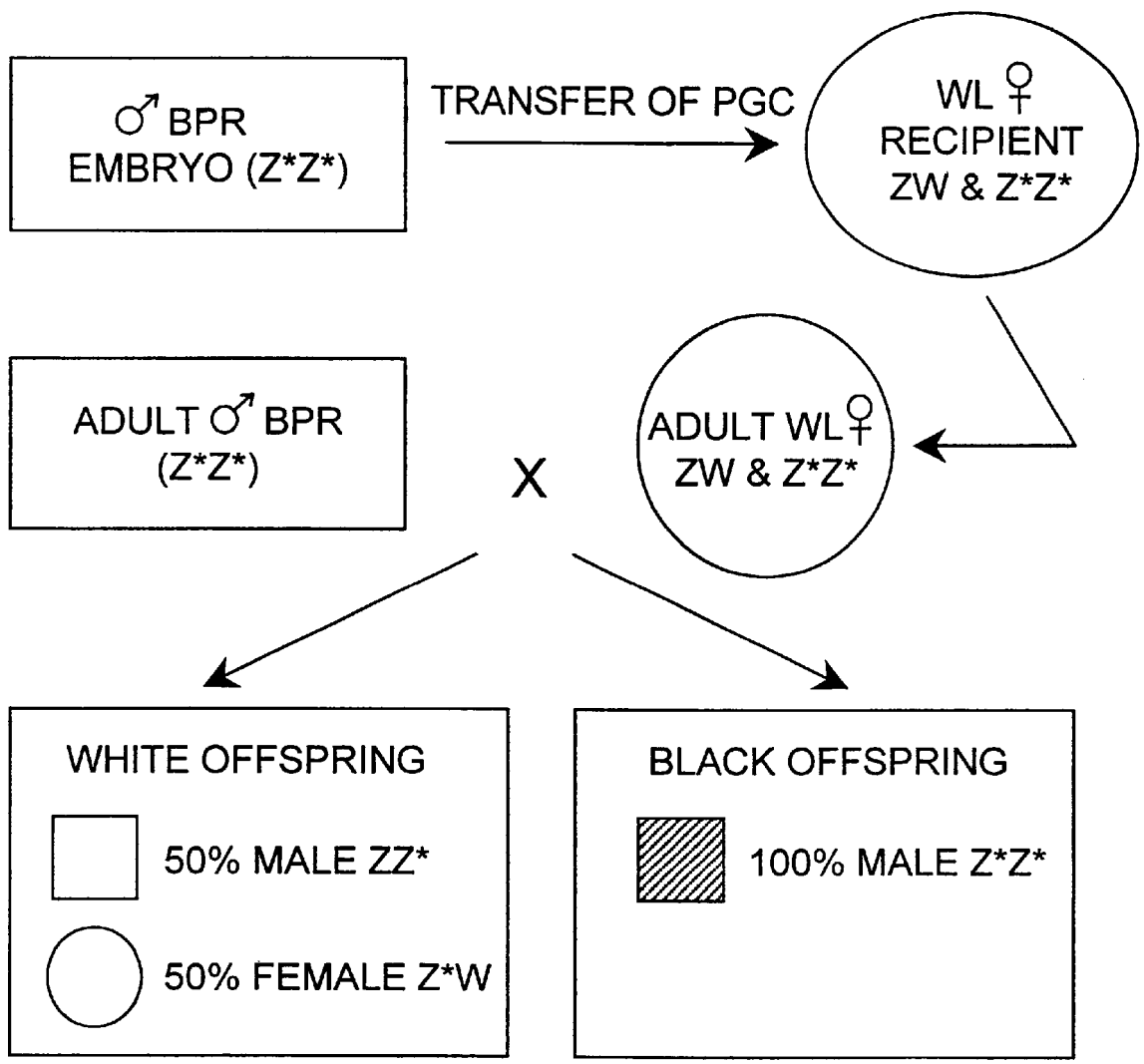
FIG. 1 presents a theoretical mating scheme for the production of an intra-specific chicken germline chimera. BPR, Barred Plymouth Rock; WL, White Leghorn. Asterisks, indicate donor gametes of BPR origin.

"Bird" or "avian species" as used herein refers to any avian species, including but not limited to chicken, turkey, duck, geese, quail, pheasant, and ostrich. Any of numerous other species can be employed to carry out the present invention, particularly when it is used for the conservation of endangered species such as the whooping crane (where the recipient is preferably a sand hill crane).

"Egg" as used herein refers to avian eggs that contain live embryonic birds.

"Primordial germ cell" or "PGC" as used herein refers to the most differentiated diploid cell line in the embryo that will ultimately develop into haploid gametes (either sperm or ova). The development, biology and use of PGCs to create germline chimeras are described in detail in D'Costa et al., Comparative Development of Avian Primordial Germ Cells and Production of Germline Chimeras (2001, 12(4): 151–168). PGCs are described in more detail hereinbelow.

"SSEA-1 antibody" refers to an antibody, preferably a monoclonal antibody, that specifically binds to the stage specific embryonic antigen-1 (SSEA-1) (M. Buehr *Exp. Cell Res.* 232, 194–207 (1997)). SSEA-1 is a carbohydrate epitope determined by galactose $\beta 1 \rightarrow 4$ fucose $\alpha 1 \rightarrow 3$ N acetylglucosamine linkage (H. Gooi et al., *Nature* 292, 156–158 (1981)). A monoclonal antibody to SSEA-1 was developed by the fusion of mouse myeloma cells with spleen cells from a mouse that had been immunized with F9 teratocarcinoma cells (D. Solter and B. Knowles, *Proc. Natl. Acad. Sci. USA* 75, 5565–5569 (1978)). SSEA-1 antibody is known as an avian immunohistochemical germ cell marker (L. Karagenc et al., *Dev. Genet.* 19, 290–301 (1996)). Particularly preferred is clone MC 480, which may be obtained from the Developmental Studies Hybridoma Bank, The University of Iowa, Iowa City, Iowa, USA.

Primordial germ cells may be provided and formulated for carrying out the present invention by any suitable technique, and stored, frozen, cultured or the like prior to use as desired. The primordial germ cells may be collected from donor avian embryos at an appropriate embryonic stage. The primordial germ cells are, in general, twice the size of somatic cells and may be easily distinguished and separated therefrom on the basis of size (e.g., by density centrifugation, filtration, immuno-affinity purification, manual selection). The primordial germ cells administered may be heterogametic (Zw) or homogametic (ZZ) depending upon the particular object of the administration. Male (or homogametic) primordial germ cells (ZZ) can be distinguished from heterogametic primordial germ cells (Zw) by any suitable technique, such as collecting germ cells from a particular donor and typing other cells from that donor, the collected cells being of the same chromosome type as the typed cells. Cells may be formulated for administration to animals by dissociating the cells (e.g., by mechanical dissociation) and intimately admixing the cells with a pharmaceutically acceptable carrier (e.g., phosphate buffered saline solution). PGCs are preferably administered in physiologically acceptable carrier, preferably at a pH of from about 6 to about 8 or 8.5, in a suitable amount to achieve the desired effect (e.g., 50, 100, 200, 500, 1000, 2000 or more PGCs per embryo). The PGCs may be administered free of other ingredients or cells, or other cells and ingredients may be administered along with the PGCs. For example, the PGCs may be isolated from somatic cells or may be administered in a relatively crude mixture of both somatic cells and PGCs (e.g., may comprises only 5% or only less of the administered cells).

The PGCs may from embryos at any suitable stage of embryonic development, e.g., from stage 4 (as classified in: V. Hamburger and H. L. Hamilton, *A Series of Normal Stages in the Development of the Chick, Journal of Morphology*, 88, 49–92 (1951); referred to as H&H stages herein), or the germinal crescent stage, through stage 30 or even stage 35 (with cells being collected from the blood or gonad in the later stages).

The PGCs may be germinal crescent PGCs, blood PGCs (also known as circulating PGCs) or gonad PGCs, as these terms are known in the art ("germinal crescent", "gonad" or "blood" referring to their tissue of origin in the original embryonic donor). In general, germinal crescent PGCs are found in stage 4 to stage 11 (H&H) embryos. Blood PGCs are generally found in the circulation of stages 12–18 (H&H) embryos, and gonad PGCs are typically found after stage 18. In embodiments of the invention, the PGCs are blood or gonad PGCs, preferably blood PGCs.

Administration of PGCs may be carried out by administering PGCs per se, or by administering precursors cells that may develop into PGCs after administration to the recipient subject. This embodiment is particularly convenient where the invention is employed to alter the sex ratio of offspring. For example, the donor cells may be blastodermal cells, which may then differentiate into primordial germ cells after introduction into the recipient bird. As used herein, the term "blastoderm" or "blastodermal cell" has its conventional meaning in the art. For example, a blastodermal cell may be found in avian embryos from about stage IV (as classified by Eyal-Giladi and Kochav, *Dev. Biol.* 49:321 (1976)); hereinafter referred to as EG&K stages) through about the time of lay (stage 1 [H&H]), or even until about stage 20 (H&H) after lay. Blastodermal cells from about stage VIII through about stage XIV (EG&K) are preferred. With respect to turkey embryos, these embryos are classified according to Gupta and Bakst (hereinafter, referred to as G&B) staging system (Gupta and Bakst, (1993) *J. Morph.* 217:313). Blastodermal cells may be found in turkey embryos from about stage VI (G&B) through the time of lay (stage 1, [H&H]), even until about stage 20 after lay (H&H).

As used herein, the terms "introducing" or "administering" PGCs to an avian subject are intended to encompass methods of "introducing" or "administering" PGCs or precursor cells that may give rise to PGCs in the recipient.

Administration of the primordial germ cells to the recipient animal in ovo may be carried out at any suitable time at which the PGCs can still migrate to the developing gonads. The PGCs may be administered during the germinal crescent, blood or gonadal PGCs stages of the recipient bird. In general, it is preferred that administration be carried out during the blood PGC stage. In other embodiments, the PGCs are introduced into the recipient bird from about stage 12 through stage 18 (H&H) of embryonic development of the recipient, more preferably stage 13 through stage 16, and most preferably stage 15. For chickens, the time of administration is thus typically during days 1, 2, 3 or 4 after lay. As discussed in more detail hereinbelow, administration of donor PGCs to the recipient bird may be delayed in embodiments of the invention in which endogenous PGCs are reduced (e.g., the recipient bird is sterilized) prior to administration of the exogenous donor PGCs.

Administration is typically by injection into any suitable target site, such as the region defined by the amnion (including the embryo), the yolk sac, the albumen, the subgerminal cavity, the coelomic cavity, or the vasculature (embryonic or extra-embryonic), etc. Injection into the embryo itself (including the embryo body wall) is preferred, and intravascular (e.g., into the dorsal aorta) or intracoelomic injection into the embryo are particularly preferred. The methods of the present invention may be carried out with or without prior reduction in endogenous PGCs (described in more detail hereinbelow). In one particular embodiment of the invention, the primordial germ cells are administered by any suitable method to a recipient subject in ovo that has not been previously sterilized. Methods in which endogenous PGCs are reduced in the recipient avian subject prior to administration of donor PGCs are discussed in more detail hereinbelow. When donor gametes are collected from the recipient, they may be collected as a mixture with gametes of both the recipient and the donor, and may be used as such a mixture or the mixture may be processed to enrich the proportion of donor gametes therein.

The methods of the invention may be practice to produce and, optionally, collect avian gametes (sperm, ova). The recipient bird containing the exogenous (i.e., donor) PGCs may be used for breeding by natural breeding methods or artificial insemination. In particular embodiments, the primordial germ cells are administered in ovo to a recipient species that is different from the donor species from which the PGCs were obtained. The recipient is then incubated to hatch and raised to sexual maturity, and sperm cells or ova of the donor species may be collected from the recipient animal (e.g., for artificial insemination), all in accordance with standard techniques. Alternatively, the bird may be allowed to breed by natural breeding methods. As one illustrative example, in the case of an endangered species, the donor avian species may be a whooping crane, and the recipient avian species may be any suitable recipient, e.g., a sand hill crane. In another example concerning commercial poultry production, the donor avian species may be a turkey, and the recipient avian species may be a chicken.

In other embodiments, both the donor and recipient species may be the same. For example, gametes from superior birds or an endangered breed may be introduced into another bird or another breed, respectively, of the same species.

As a further possibility, the donor cells may first be genetically modified (e.g., to introduce a heterologous sequence and/or to disrupt or "knock out" an endogenous gene or sequence) prior to administration to a recipient bird, which recipient may be from the same or a different species as the donor PGCs.

The invention may also be employed to increase the proportion of Z or W gametes produced by an avian subject. In particular embodiments, the inventive methods may be used for increasing the number or ratio of male gametes (Z genotype) and, accordingly, male birds in a group of eggs. For example, in embodiments of the invention, the present invention involves administering to a female bird in ovo male avian primordial germ cells (ZZ genotype). The gender of the recipient bird may be predetermined or determined after hatch. The bird is then incubated to hatch, the gender of the bird determined if necessary, raised to sexual maturity, and bred by crossing the recipient female bird with a suitable male breeder stock in accordance with known techniques. A plurality of fertile eggs laid by the recipient female bird are then collected, and optionally incubated to hatch with the resulting birds grown for at least two to three weeks (e.g., commercial poultry raised for meat). In embodiments of the invention, the ratio of male (Z) to female (w) gametes produced from the female bird is greater than that obtained in the absence of administering the male primordial germ cells to the female bird in ovo. Likewise, according to embodiments of the invention, the ratio of male to female bird eggs (or birds) produced from the female bird is greater than that obtained in the absence of administering the male primordial germ cells to the female bird in ovo. Such methods are typically used in species of bird that are raised for meat production, such as chickens, turkeys, ducks, quail, geese, and the like.

Those skilled in the art will appreciate that the donor PGCs may be genetically modified prior to administration to the recipient bird, e.g., by gene disruption and/or to introduce one or more heterologous nucleotide sequence(s). Methods of transiently or stably introducing a heterologous sequence into avian cells are known in the art (e.g., U.S. Pat. No. 5,162,215 to Bosselman et al.). Preferably, the heterologous nucleotide sequence is stably incorporated into the PGC. Means for introducing nucleic acids of interest into recipient cells are known and include lipofection, transfection, microinjection, transformation, microprojectic techniques, etc. Any suitable vector may be used, including plasmids, viruses (including retroviruses), phage, and the like, whether in native form or derivatives thereof.

The donor PGCs may be genetically modified so as to produce a desired result in the recipient bird (e.g., to express a transgene that effects sex determination). Alternatively, it may be intended that the genetic modification be passed on to the offspring of the chimeric bird and produce a desired effect therein.

Introduction of one or more heterologous nucleotide sequence(s) (e.g., a foreign sequence or an extra or modified copy of an endogenous sequence) may be used in a variety of applications, e.g., to produce a polypeptide of interest in the bird (e.g., in the plasma or eggs of such birds for convenient collection and purification). According to this embodiment, the bird may be used essentially as a bioreactor. Polypeptides of interest include therapeutic (e.g., for veterinary or medical uses) or immunogenic (e.g., for vaccines) polypeptides, antibodies (including antibody fragments and single chain antibodies), enzymes (e.g., industrial enzymes), hormones and growth factors, or any other protein of interest.

Alternatively, the polypeptide may be a reporter polypeptide that serves as a marker of the donor cells (e.g., Green Fluorescent Protein, β-galactosidase, alkaline phosphatase, β-lactamase, neomycin phosphotransferase, and chloramphenicol acetyltransferase).

In other embodiments, the polypeptide is a therapeutic or immunogenic polypeptide or any other polypeptide that has a desired or beneficial effect on the recipient bird, e.g., a polypeptide that that has a desired phenotypic effect or enhances growth performance (including increased muscling and/or reduced fat deposition and/or improved feed to gain ratio), egg production, disease tolerance, and the like.

As a further alternative, the heterologous nucleic acid of interest may encode an antisense nucleic acid, a ribozyme (e.g., as described in U.S. Pat. No. 5,877,022) or any other nontranslated RNA.

It will be understood by those skilled in the art that the heterologous nucleotide sequence(s) of interest may be operably associated with appropriate control sequences. For example, the heterologous nucleic acid may be operably associated with expression control elements, such as transcription/translation control signals, origins of replication, polyadenylation signals, and internal ribosome entry sites (IRES), promoters, enhancers, and the like.

It will further be appreciated that a variety of promoter/enhancer elements may be used depending on the level and tissue-specific expression desired. The promoter/enhancer may be constitutive or inducible, depending on the pattern of expression desired. The promoter/enhancer may be native or foreign and can be a natural or a synthetic sequence. By foreign, it is intended that the transcriptional initiation region is not found in the wild-type host into which the transcriptional initiation region is introduced. In particular embodiments, the heterologous nucleotide sequence(s) is operatively associated with the ovalbumin promoter or the lysozyme promoter.

Promoter/enhancer elements that are native to the target cell or subject to be treated are most preferred. Also preferred are promoters/enhancer elements that are native to the heterologous nucleic acid sequence. The promoter/enhancer element is chosen so that it will function in the target cell(s) of interest. Avian promoter/enhancer elements are also preferred. The promoter/enhance element may be constitutive or inducible.

Inducible expression control elements are preferred in those applications in which it is desirable to provide regulation over expression of the heterologous nucleic acid sequence(s). Inducible promoters/enhancer elements for gene delivery may be cell- or tissue-specific promoter/ enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metal-othionein promoter.

In embodiments wherein which the heterologous nucleic acid sequence(s) will be transcribed and then translated in the target cells, specific initiation signals are generally required for efficient translation of inserted protein coding sequences. These exogenous translational control sequences, which may include the ATG initiation codon and adjacent sequences, can be of a variety of origins, both natural and synthetic.

In particular embodiments of the invention, the number of endogenous PGCs in the recipient bird is reduced prior to introduction of the donor PGCs. In this manner, the donor PGCs may repopulate the gonads of the recipient bird and may increase the efficiency of producing chimeric birds and the proportion of gametes (and offspring) that are derived from the donor bird. The endogenous PGCs may be reduced by at least about 40%, 50%, 60%, 70%, 80%, 90%, 95%, 98% or even more. In other particular embodiments, the recipient bird is essentially sterilized, as that term is defined above. The targeted reduction in endogenous PGC number in the recipient bird may be based on a number of considerations, including: the desired number and proportion of gametes to be derived from the donor bird, minimization of any adverse effects associated with the method of achieving endogenous PGC reduction, and the like.

Alternatively stated, the invention may be practiced so that the ratio of gametes (and/or offspring) derived from the donor PGCs as compared with the recipient bird's PGCs may be about 60/40, 65/35, 70/30, 80/20, 90/10, or higher. In particular embodiments, the invention may be practiced so that fewer than 50% of the gametes (and/or offspring) are derived from the donor PGCs. A relatively low proportion of gametes and/or offspring derived from donor PGCs may be acceptable in those applications in which only a relatively small number of donor gametes and/or chimeric offspring are necessary and/or the donor gametes and/or chimeric offspring are commercially valuable.

The reduction in endogenous PGCs may be achieved by any suitable method known in the art. For example, continuous exposure (20 days) to gamma irradiation (0.3–3.4 R/hr, $^{60}$Co) resulted in the complete destruction of oocytes at a dosage level of 3.4 and 1.8 R/hr (Mraz and Woody, *Radiation Research* 54:63–68 (1973)). Short-term exposure to a gamma source has also been described (Carsience et al., *Development* 117:669–75 (1993); Thoraval et al., *Poultry Sci.* 73:1897–1905 (1994); Maeda et al., *Poultry Science* 77:905–07 (1998)). In these studies, unincubated eggs were exposed to 500–700 rads just prior to the injection of stage X blastodermal or area pellucida cells. Sterilization of embryos using ultraviolet light has been described (Reynaud, *J. Embryol. Exp.Morphol.* 21:485–507 (1969);

Reynaud, J., *Roux's Archives of Developmental Biology* 179:85–110 (1976); Aige-Gil and Simkiss (*Brit. Poul. Sci.* 32:427–438 (1991)). One drawback to this approach is that it results in a relatively high incidence of developmental abnormalities, which may limit the application of this approach.

In a particular preferred embodiment, busulfan (1,4-butanediol dimethane sulfonate, BU) is administered to the recipient bird to reduce endogenous PGC number. BU has previously been reported to reduce PGC number in avian (see, e.g., Swartz, *Teratology* 21:1–8 (1980); Hallett and Wentworth, *Poultry Science* 70:1619–23 (1991); Aige-Gil and Simkiss, *Brit. Poul. Sci.* 32:427–438 (1991); Vick et al., *J. Reproduction & Fertility* 98:637–41 (1993); Bresler et al., *British Poultry Science* 35:241–47 (1994)) and mammalian (see, e.g., Hemsworth and Jackson, *J. Reproduction & Development* 6:229–33 (1963); Kim et al., *Molecular Reproduction and Development* 46:515 (1997); Hirshfield, *Biology of Reproduction* 50:421 (1994)) embryos. BU has also been used as a chemotherapeutic agent for the treatment of leukemia (Bhagwatwar et al., *Cancer, Chemotherapy & Pharmacology* 37:401 (1996)).

The dosage of BU to be administered will generally be dependent upon the desired outcome, the species of bird, and the age and condition of the embryo, site of administration within the egg, and the like. While higher doses may be more effective in achieving sterilization, BU has also been found to be teratogenic, resulting in developmental defects. In some application, only modest reductions in PGC number or, conversely, relatively high levels of developmental defects, may be tolerated depended on the intended purpose. Suitable dosages of BU may be as low as about 10, 20, 30, 40 or 50 μg/egg or as high as about 70, 80, 90, 100, 125, 150 or 200 μg/egg. Generally, a range of from about 50 to about 100 μg BU per egg is suitable for achieving a reduction in PGC number without undue teratogenic effects. Higher dosages of BU have been reported (e.g., as high as 200 to 400 μg) when the BU is administered at a distant site in the egg from the embryo, such as into the albumen. However, in general it will be preferred to administer the BU relatively close to the embryo. In addition, because of the potential deleterious effects of BU on the donor PGCs, it will generally be preferred to administer a smaller dosage in relatively close proximity to the embryo so that there is sufficient clearance prior to administration of donor PGCs.

The present inventors have observed inconsistent results upon administration of an aqueous BU composition, or in combination with a sesame oil carrier, to chick embryos. While not wishing to be bound by any particular theory, it appears that variability may be attributable, at least in part, to the fact that BU is relatively insoluble and forms a suspension in aqueous solutions (see, e.g., Hallett and Wentworth, *Poultry Science* 70:1619–23 (1991)). Accordingly, in particular embodiments, the BU may be advantageously administered as an emulsion. Emulsions of BU may be formed by adding an organic agent, such as dimethyl formamide (DMF), dimethyl sulphoxide (DMSO), demethylacetamide (DMA), and the like. In preferred embodiments, the BU emulsion contains BU and DMF.

Alternatively, or additionally, the BU composition may contain a non-toxic oil, such as sesame oil, vegetable oil (e.g., corn oil, canola oil, and the like) peanut oil, or any other suitable oil. The oil serves as a vehicle and is believed to help stabilize an emulsion after administration to the egg and to float the BU composition to the surface of the egg, bringing the BU in contact with the embryo.

In one particular embodiment of the invention, the BU is administered as an emulsion with DMF and oil.

Hirshfield, *Biology of Reproduction* 50:421 (1994) have described the administration of BU mixed with DMSO and sesame oil to pregnant rats for the purpose of reducing the stockpile of primordial follicles in the developing ovary in female offspring so as to study the relationship between the size of the stockpile of primordial follicles and the rate at which follicles move into the growing pool (see, Abstract). Kim et al., *Molecular Reproduction and Development* 46:515 (1997) administered BU in a mixture with DMF and sesame oil to male rats and pigs to reduce the number of developing male germ cells. The remaining early-stage male stem cells were then transformed with a liposome/DNA complex (containing a LacZ construct) to produce genetically modified spermatozoa.

As far as the present inventors are aware, there are no reports in the literature describing administration of an emulsion of BU, DMF, and sesame oil to avian species in ovo to reduce PGCs.

The total volume of the BU composition to be administered to the egg is not critical as long as it is not so large as to unduly harm the embryo. Typical volumes are less than about 50, 100, 200 or 300 µl.

The BU composition may be administered to any suitable target site, such as into the yolk sac, the region defined by the amnion (including the embryo), the albumen, the subgerminal cavity, the coelomic cavity, or the vasculature (embryonic or extra-embryonic), etc. Injection into the yolk sac or the embryo itself (including the embryo body wall) is preferred. In embodiments of the invention, the egg is placed horizontally (e.g., for 1–4 hours), and a delivery device is inserted through the blunt end of the egg (i.e., substantially horizontally) and into the yolk, and the BU composition is delivered through the device into the yolk beneath the embryo.

The time of delivering the BU composition is not critical as long as the concentration is sufficiently reduced by the time that the donor cells are introduced into the egg so that the residual BU in the egg does not have an unduly adverse impact (e.g., by impairing the viability) on the donor PGCs. In embodiments of the invention, it is preferred that the egg contain less than about 30 µg, 25 µg, 20 µg, 15 µg, 10 µg, 5 µg, 2.5 µg, 1 µg, or 0.5 µg BU at the time that the donor PGCs are introduced into the egg. In some embodiments, there is essentially no detectable BU remaining in the egg.

The half-life of BU is approximately 10 hours. It will be appreciated by those skilled in the art that the initial dosage of BU and/or the delay between administration of the BU and the donor PGCs may be selected so as to achieve a sufficiently low dosage of residual BU (i.e., due to clearance) at the time the donor PGCs are introduced into the egg.

In embodiments wherein the embryo is exposed to BU so as to reduce endogenous PGCs, the donor PGCs will typically be administered during the blood PGC stage, e.g., from about stage 12–18 (H&H), alternatively stated, in chickens from about 2 to 3 days after lay. In particular embodiments, the donor PGCs may be administered at least about 48 hours after the BU composition. According to this embodiment, if 75 µg BU is administered at 24 hours after lay, the dosage will be reduced to about 2.3 µg by 3 days after lay. Alternatively, if only 25 µg of BU is administered (e.g., at 24 hours or 48 hours after lay), the donor PGCs may be administered approximately 24 hours later.

The in ovo administration of the primordial germ cells may be carried out by any suitable technique, either manually or in an automated manner. Injection is preferred. The mechanism of in ovo administration is not critical, but it is preferred that the method not unduly damage the tissues and organs of the embryo or the extraembryonic membranes surrounding it so that the treatment will not unduly decrease hatch rate. A hypodermic syringe fitted with a needle of about 18 to 26 gauge is suitable for the purpose. Depending on the precise stage of development and position of the embryo, a one-inch needle will terminate either in the fluid above the chick or in the chick itself. A pilot hole may be punched or drilled through the shell prior to insertion of the needle to prevent damaging or dulling of the needle. If desired, the egg can be sealed with a substantially bacteria-impermeable sealing material such as wax or the like to prevent subsequent entry of undesirable bacteria. It is envisioned that a high speed injection system for avian embryos will be particularly suitable for practicing the present invention. Numerous such devices are available, exemplary being the EMBREX INOVOJECT™ system (described in U.S. Pat. Nos. 4,681,063 and 4,903,625 to Hebrank), and U.S. Pat. Nos. 4,040,388; 4,469,047, and 4,593,646 to Miller. The disclosure of all United States patent references cited herein are be incorporated herein by reference in their entirety. All such devices, as adapted for practicing the present invention, comprise an injector containing the a formulation of the primordial germ cells as described herein, with the injector positioned to inject an egg carried by the apparatus in the appropriate location within the egg as discussed above. In addition, a sealing apparatus operatively with the injection apparatus may be provided for sealing the hole in the egg after injection thereof.

The present invention is described in greater detail in the following non-limiting Examples.

EXAMPLE 1

Plasmid Isolation and Verification

Matzke et al. (*Chromosoma* 102:9–14 (1992)) have characterized a repetitive DNA sequence that is enriched on the turkey microchromosomes. It is a 41 bp repeat element represented on 5% of the genome (approximately $2.2 \times 10^6$ copies in diploid genome of a cell). Hence, this species-specific DNA sequence was used in DNA-DNA hybridization to test if it could be used to identify turkey DNA in chick embryos.

DH5α cells transformed with the TM1 plasmid carrying the turkey specific repeat element (Matzke et al., (1992) *Chromosoma* 102:9) were provided by Dr. M. Matzke were streaked onto LB plates containing the antibiotics ampicillin (20 µg/ml)+methicillin (80 µg/ml) and grown overnight at 37° C. Six individual colonies were picked and grown overnight in 10 ml LB containing the above antibiotics. Plasmid DNA was isolated from the 6 different colonies using the Qiagen mini prep protocol. To verify the identity of the plasmid the undigested plasmids, linearized plasmid (EcoR I) and the double-digest (EcoR I+Hind III) were separated on a 2% agarose gel. Two of the six colonies containing the insert were subsequently used for large scale plasmid isolation (Qiagen). The undigested parent plasmid (puc18), undigested recombinant plasmids, linearized plasmid (EcoR I/Hind III/BamH I) and double-digested plasmid (EcoR I+Hind III and EcoR I+BamH I) were separated on 2% gel to confirm the identity of the plasmid isolated.

EXAMPLE 2

PCR Labeling of TM1 Probe

A pair of primers was synthesized based on their ability to amplify the insert in the multicloning site of the parent puc18 plasmid. They were M13 puc reverse=5'AAC AGC TAT GAC CAT G (SEQ ID NO:1) and M13 puc forward= 5'GTA AAA CGA CGG CCA GT (SEQ ID NO:2). The optimized PCR mixture consisted of 3 mM $MgCl_2$ in Taq buffer (Idaho Tech) 0.5 μM each primer, 50 ng of DNA (TM1) circular denatured plasmid, 5 units of Taq polymerase (Promega), 10 μl of PCR dig-labeling mix (Boehringer Mannheim). The reaction volume was made up to 100 μl with sterile water, PCR conditions consisted of an initial denaturation at 96° C. for 5 min followed by 30 cycles consisting of denaturation (94° C.) for 45 seconds, annealing (50° C.) for 55 seconds followed by extension at 72° C. for 60 seconds. The PCR was performed in "The Mini Cycler" Model PTC 150 (MJ Research Inc., Massachusetts). After amplification the entire sample was electrophoresed on a 2% gel. The labeled insert was eluted from the gel using the Qia quick gel extraction kit (Qiagen) according to manufacturer recommendations. The probe was stored at −20° C. and used for dot blot and in situ hybridization. Prior to storage the yield of the DIG-labeled DNA was estimated according to the Genius system user's guide for filter hybridization (Boehringer Mannheim).

EXAMPLE 3

Dot Blot Hybridization

To verify the accuracy, sensitivity and specificity of the TM1 insert, serial dilution of male and female turkey DNA (0–500 ng), chicken male and female DNA (0–2 μg) and parent plasmid containing the TM1 insert (10 ng–1 pg) were denatured and spotted onto nitrocellulose paper. The blot was baked at 80° C. for an hour and then used for hybridization. Prehybridization and hybridization were carried out using the Engler-Blum procedure (*Anal Biochem*. 210:235–244 (1993)). Hybridization was carried out overnight at 68° C.; probe concentration used was 2.5 ng cDNA probe/ml. After hybridization and stringency washes the blot was placed in washing buffer (0.1M Maleic Acid, 0.15 M NaCl pH 7.5). The membrane was incubated in blocking solution (wash buffer+3% Tween 20) for 30 minutes and then placed in blocking solution containing anti-digoxigenin alkaline phosphatase conjugate for half an hour. The membrane was subsequently washed in washing buffer twice and then incubated in detection buffer (0.1 M Tris HCl, 0.1 m NaCl, 50 mM $MgCl_2$ pH 9.5). Hybrids were finally detected using the chemiluminescent substrate CDP-STAR™ (from Boehringer-Mannheim, Germany). Blots were exposed to X-ray film for at least 5 minutes.

EXAMPLE 4

Production of Interspecific Turkey-chicken Embryonic Germline Chimeras

Fertilized turkey eggs were incubated at 38.5° C. for 8–8.5 days (stage 27–28 H&H). Embryos were dissected to obtain gonads. The gonads were collected in DMEM and 10% FBS and dispersed by passing them through a 30-gauge needle. The cells were cultured in DMEM and 10% FBS until confluence (3–5 d). The stromal cells dispersed and formed a confluent layer while the germ cells were loosely attached to the stromal cells. The germ cells were collected by gentle pipetting and counted. Approximately 150–300 cells in 3–5 μl of medium were injected into the sinus terminalis of 60 or 72-hour chick embryos. The embryos were then incubated in 100-mm petri dishes or in their own eggshells at 38.50° C. for 2–5 days. After incubation, DNA was isolated from the embryos (n=18) and used for dot blot analysis with the dig-labeled probe TM1.

EXAMPLE 5

In Situ Hybridization

The in situ hybridization was performed on paraffin sections and cryosections. This procedure is based on the protocol by Rolighed and Lindeberg (see J. Rolighed, Detection of HPV II DNA in paraffin—embedded laryngeal tissue with a DIG-labeled DNA probe. In *Non-radioactive In Situ Hybridization Application Manual Boehringer Mannheim Second Edition*, pp 122–125 (1996)) with some modifications.

Paraffin Sectioning: Gonads were isolated from turkey embryos (day 9) and chick embryos at corresponding stages, fixed overnight in 4% paraformaldehyde at 4° C. The gonads were washed in PBS three times for a total of 90 minutes. They were the dehydrated, embedded in paraffin and sectioned (10 microns). Sections were collected on Probe—On Plus™ slides (Fisher Scientific). The sections were baked at 60° C. for 30 minutes, dewaxed in xylene and rehydrated through graded ethanol series (99%–water). The sections were treated with Proteinase K (50 μg/ml and 100 μg/ml) in TES (50 mM Tris HCl pH 7.4, 10 mM EDTA and 10 mM NaCl) for 12 to 25 minutes at 37° C. and at room temperature.

Cryosectioning: The trunk region of day 8.5 turkey embryos was fixed overnight at 4° C. in 4% paraformaldehyde in PBS. Varying concentrations of proteinase K in TES from 0 to 45 μg/ml for 10, 15 or 20 minutes at 37° C. were tested. The 0.67 μg/ml and 1.25 μg/ml at 37° C. for 15 min was the optimal proteolytic treatment for the embryonic tissues Preparation of probe/blind cocktail: The probe cocktail consisted of 10 μl of 50×Den harts solution, 50 μl of dextran soleplate (50%), 10 μl of salmon sperm DNA (9.4 mg/ml), 100 μl of 20×SSC, 500 ng of digoxigenin labeled TM1 probe and distilled water was added for a final volume of 250 μl. Finally 250 μl of formamide was added to the cocktail. The blind cocktail contained all the above components except the labeled TM1 probe. The cocktail was mixed by vortexing and stored at −20° C.

Hybridization: After proteolytic digestion both the paraffin and cryosections were fixed in 0.4% paraformaldehyde for 5 minutes at 4° C. The sections were then washed in distilled water (5 minutes) and air-dried. Then 10 or 15 μl of probe cocktail or blind cocktail (negative control) was added over each section. Siliconized cover slips were placed on the sections prior to denaturation at 95° C. for 6 minutes. The slides were then placed for a minute on ice and placed in a humid chamber for 16–20 hours at 42° C. The stringency washes and detection of the hybrid was similar to that described by Rolighed and Lindeberg (see above), except the ready-made alkaline phosphatase substrate NBT/BCIP (Amresco) was used for detection of hybrids. After detection, slides were counter stained with aqueous eosin for a few seconds and washed. Samples were mounted in an aqueous mounting medium made from 10 grams of gelatin dissolved in 60 ml of water at 70° C.–80° C. to which 70 ml of glycerin and 1 ml of phenol was added.

EXAMPLE 6

Production of Interspecific Chicken-turkey Embryonic Chimeras

Barred Rock chicken embryos were incubated until stage 23–25 (H&H). The genital ridges along with some of the adjoining tissue from ten embryos was collected in DMEM, supplemented with 10% FBS, glutamine, antibiotic and antimycotic solution. They were then rinsed twice in PBS and incubated in 0.02% EDTA at 37° C. for fifteen minutes. Fresh media was added and the ridges were teased using needles. The entire cell suspension was collected in a 15 ml tube and the clumps were allowed to settle for a couple of minutes. The cell suspension was collected and spun at 1500 rpm for 5 minutes. The media was replaced and cell viability determined using trypan blue exclusion. Aliquots of the cell suspension were taken and stained with SSEA-1 antibody to determine the number of germ cells injected. Approximately 5 μl of cell suspension containing 25–30 PGCs (percentage of PGCs in cell suspension was approximately 3.2%) were injected into the blood vessel of each Nicholas turkey embryo (n=10) at stages 13–14 (H&H) of development. The embryos were incubated in glass dishes covered with plastic wrap at 37.5° C. until stages 21–25. The entire trunk region of the recipient embryos was fixed in 4% paraformaldehyde overnight at 4° C., washed thrice in PBS for a total time of 90 min, embedded in gelatin/sucrose, frozen and sectioned.

As turkey gonadal PGCs are SSEA-1 negative and chicken gonadal PGCs are SSEA-1 positive, the antibody against SSEA-1 can be used to identify the transfer donor chick PGCs in the embryonic germline chimeras.

EXAMPLE 7

Production of interspecific Turkey-chicken Embryonic Germline Chimeras

Fertilized turkey eggs were incubated at 38.5° C. for 8–8.5 days (stage 27–28 H&H). Embryos were dissected to obtain gonads. They were collected in PBS and incubated in 0.02% EDTA at 37° C. for twelve minutes. Fresh media was added and the ridges were teased gently using needles. The entire cell suspension was collected and spun at 1500 rpm for 5 minutes. The media was replaced and cell viability determined. The entire cell suspension was preplated at 37° C. in DMEM+10% FBS for 6–7 hours. After culture the non-adherent cells were gently collected and centrifuged. Then 2–3 μl of cell suspension containing approximately 150 PGCs was injected into the blood vessels stage 14 (H&H) chick embryos. The recipient eggs were sealed and incubated at 37.5° C. Recipient embryos were collected at different stages of incubation from stage 19 until stage 25. The embryos were rinsed in PBS thrice and then fixed in 4% paraformaldehyde overnight at 4° C. They were washed thrice in PBS; the total time varied depending on the thickness of the embryo. The embryos were placed in 50% ethanol and embedded in paraffin. The sections were dewaxed, rehydrated and rinsed in PBS.

The controls for the double staining technique (see below) were transverse sections of two stage 26 chick embryos and two stage 24-turkey embryos. Forty-two sections of the chick genital region and all serial sections of the turkey genital region were stained.

A total of eight recipient chick embryos were serially sectioned. Five of the eight embryos were fixed at stages 19 & 20. Two embryos were fixed at stage 22 & 23. The last embryo was fixed at stage 25. A majority of the stage 19 & 20 sections were used for double staining. Only the alternate sections of stage 22, 23 and 25 embryos were used for the double staining.

EXAMPLE 8

Double Staining With SSEA-1 Antibody and PAS Stain

Immunohistochemical studies were carried out using the Vectastain ABC-AP kit (Vector Laboratories, Burlingame, Calif.). Sections were rinsed thrice in PBS for a total time of 30 minutes. They were then blocked in 1.5% goat serum in PBS for 20 minutes to eliminate nonspecific binding. Subsequently, sections were incubated for an hour in primary monoclonal antibody against SSEA-1 (clone MC 480 obtained from the Developmental Studies Hybridoma Bank, The University of Iowa, Iowa City, Iowa). After a rinse in PBS, embryonic sections were incubated in biotinylated secondary antibody (30 min) then rinsed in PBS and incubated in Vectastain ABC-AP reagent (30 min). After a final wash in PBS they were stained in the alkaline phosphatase substrate NBT/BCIP (Amresco, Solon, Ohio) for 20 min.

Following immunohistochemical staining the sections were rinsed in tap water and placed in periodic acid for 6 min. The sections were then rinsed in water for 10 min and stained in Schiff reagent for 15 min. After rinsing them in tap water the sections were mounted in the aqueous mounting medium.

EXAMPLE 9

Plasmid Isolation and Verification

Based on gel electrophoresis analysis, the parent plasmid: puc18 was 2.69 kb while the linearized recombinant plasmid obtained from Dr. Matzke was approximately 2.8 kb long. Double-digestion of the plasmid DNA from colonies number 2 and 5 released an insert of approximately 0.15–0.17 kb. This verified that the transformed DH5 cells sent to us contained the appropriate recombinant plasmid. The plasmid contained the TM1 fragment (149 bp) consisting of three copies of the turkey-specific 41 bp repeat.

EXAMPLE 10

PCR Labeling of TM1 Probe

PCR amplification of circular plasmid DNA along with digoxigenin—labeled nucleotides resulted in the production of an amplification product of approximately 0.19–0.20 kb. The increase in size of the amplification product compared to the insert (0.15–0.17 kb) is probably due to incorporation of multiple DIG-labeled nucleotides. The PCR labeled probe was subsequently used in both the dot blot hybridization experiments and DNA-DNA in situ hybridization.

EXAMPLE 11

Dot Blot Hybridization

The results of the Dot Blot Hybridization (data not shown) indicated the probe bound to both male and female turkey DNA samples with equal intensity. Thus verifying that the probe is not sex-specific. Hybridization was done on serial dilutions of turkey DNA from 500 ng to 0 ng of turkey DNA. The probe detected as low as 0.30 ng of turkey DNA. Hybridization with 0 to 2 micrograms of male as well as female chicken DNA confirmed that the probe was species-specific and it did not bind to chicken DNA. Varying concentrations of turkey DNA (10 ng–0 ng) was mixed with 0–2 μg of chicken DNA. Hybridization with this mixture of DNA indicated that as little as 1.25 ng of turkey DNA could be detected in 1 μg of chicken DNA.

EXAMPLE 12

Production of Interspecific Turkey-Chicken Embryonic Germline Chimeras

No interspecific turkey-chicken embryonic germline chimeras could be detected using the above dot blot hybridization protocol. The inability to detect chimeras could be due to an intrinsic biological barrier that would prevent migration of turkey gonadal PGCs to the chicken gonad. It could also be due to a technical problem, i.e., the procedure (dot blot hybridization) was not sufficiently sensitive to identify the few donor germ cells in the chicken gonad. The latter reason seemed more likely; hence, an attempt was made to develop a more sensitive technique, i.e., in situ hybridization to localize the donor PGCs in the recipient.

EXAMPLE 13

In Situ Hybridization Analysis of Turkey Sections

Theoretically, the in situ marker system would be an appropriate marker for identifying donor (turkey) cells in a chimera. As the marker is within the nuclei, it is ubiquitous and does not leak out to other cells or affect development of the recipient embryo. In the present study, the TM1 sequence selectively bound to DNA in turkey nuclei (data not shown). No positive signal was detected in chicken cells (data not shown) or sections incubated with blind cocktail (data not shown), indicating that the probe was species-specific and without non-specific signal. Ideally in the positive control sections of turkey embryos every nucleus should have stained positive. However, only a small percentage of cells stained positive (data not shown). In addition, there was variation in the signal intensity between different cell populations in the same section under identical digestion conditions. This indicated that there were false negatives associated with this technique. A decrease in the percentage of false negatives might be accomplished by lowering the stringency conditions. However, this could also lead to false positives. In embryonic germline chimeras the donor cells would represent a very small percentage of the total embryonic section or cells. In addition, this marker system identifies only a minority of positive turkey cells. Hence, in situ hybridization with the TM1 probe would not be an efficient way of identifying chimeras.

EXAMPLE 14

Identification of Interspecific Chicken-turkey Embryonic Chimeras Using SSEA-1 Staining In order to confirm that there were not technical problems associated with the procedure, interspecific chicken-turkey germline chimeras were produced by the intravascular transfer of chicken gonadal germ cells. As there is a species difference in the expression of the SSEA-1 antigen on chick and turkey gonadal PGCs, it was hypothesized that SSEA-1 antibody could be used to identify chicken-turkey embryonic germline chimeras. Of the five embryos that survived, four were cryosectioned. In one of the four embryos, nineteen SSEA-1 positive cells were identified in the dorsal mesentery of the turkey embryos (data not shown), an additional four SSEA-1 labeled chick germ cells were identified in the turkey genital ridge (data not shown). In the second embryo, two SSEA-1 positive cells were identified in the vicinity of the gonad. In the remaining two embryos, no donor PGCs were identified.

Based on these results gonadal PGCs from day 5 chick embryos (stage at which PGCs are SSEA-1 positive) when injected intravascularly into a stage 13 turkey embryo are capable of remigration, colonizing the gonad and giving rise to germline chimeras. Thus, it appears that the chemoattractant produced by the turkey gonad is not species-specific. It also reconfirmed that chicken gonadal PGCs retain their ability to migrate even after they have colonized the gonad. The lower efficiency of germline chimeras in this study could be due to the lower number of donor PGCs in the injected cell suspension.

EXAMPLE 15

Identification of Interspecific Turkey-chicken Embryonic Chimeras Using SSEA-1 and PAS Staining Previous research has identified a species difference in the expression of SSEA-1 by turkey and chick PGCs. This antigenic variation coupled with the standard PAS test could potentially be used for identifying turkey-chick germline chimeras. Observations of the double stained chick embryonic sections verified that chick PGCs are both PAS positive and SSEA-1 positive (data not shown). No PAS positive, SSEA-1 negative germ cells were observed in the chick control sections. Double staining of the stage 24 turkey sections with PAS and SSEA-1 verified that turkey PGCs migrating through the dorsal mesentery and colonizing the gonad are PAS positive and do not express the SSEA-1 epitope (data not shown). Hence, double staining of chick and turkey embryos verified that the double staining technique could be used as a marker for identifying turkey germ cells in a chick gonad. Using the SSEA-1 antibody along with the standard PAS stain, germline chimeras were detected in four out of eight recipient chick embryos (Table 1). Approximately 24 hours after injection of turkey PGCs into the blood vessels of chick embryos SSEA-1 negative and PAS positive turkey germ cells were identified in the chick embryos. Turkey PGCs were identified along with the chick PGCs in the thickened coelomic epithelium (data not shown). The epithelium was located in between the coelomic angle and the mesonephros, the site of the future gonad. In the older embryos (stage 22 and 23) donor turkey PGCs were observed in both recipient chick embryos. Some germ cells were located in the dorsal mesentery (data not shown), others had migrated further and had colonized the chick gonad (data not shown). Analysis of potential chimeras with the double staining technique verified that turkey gonadal PGCs can be used to produce interspecific chimeras.

TABLE 1

Production of turkey - chicken embryonic germline chimeras

| Stage | No. of Embryos Sectioned | No. of Germline Chimeras |
|---|---|---|
| 19/20 | 5 | 2/5 |
| 22/23 | 2 | 2/2 |
| 25 | 1 | 0/1 |

Although the DNA-DNA hybridization was species-specific, the procedure was unable to detect chimeras. The dot blot hybridization procedure was not sensitive enough to identify the donor PGCs whereas the in situ hybridization procedure had a high percentage of false negatives associated with it. The double staining procedure appears to be a successful way of identifying turkey-chicken chimeras. Based on the above results, gonadal PGCs from chick and turkey embryos when injected intravascularly are capable of remigration to the gonad and giving rise to germline chimeras. Thus, it appears that the chemoattractant produced by the avian gonad is not species-specific. It also confirms that gonadal PGCs retain their ability to migrate even after they have colonized the gonad.

EXAMPLE 16

Reduction in Endogenous PGCs Following Administration of a Busulfan Emulsion Chicken embryos were treated with busulfan to reduce endogenous PGCs.

A. Preparation of busulfan Emulsion:

Fifteen mg of busulfan was dissolved in 5 ml of dimethyl formamide (DMF) in a glass vial. Five ml of sesame oil was added to the solution. The mixture was vortexed completely to create an emulsion. The concentration of busulfan was 1.5 µg/µg in the emulsion. Fresh busulfan emulsion was prepared for each batch of injections.

B. Injection of Busulfan Emulsion:

The fertilized eggs were incubated at 37.5° C., 60% relative humidity for 22 hours. Then the eggs were placed horizontally in the incubator for 2 hours. The blunt end of each egg was cleaned with 70% ethanol. Using a curved forceps, a small hole was then made in the shell covering the air chamber, without damaging the outer shell membrane. Fifty µl of busulfan emulsion (containing 75 µg busulfan) was injected horizontally through the air chamber into the yolk using a hypodermic needle (21 G×1.5 inch). The emulsion was vortexed completely before use. The eggs were kept horizontal for the entire injection procedure. The hole in the shell was sealed with scotch tape. The eggs were incubated vertically after injection.

C. Assessment of Sterility:

The embryos were collected at stage 27 (H&H) and fixed in 4% paraformaldehyde overnight at 4° C. The embryos were embedded in paraffin, sectioned at 7 µm thickness and stained immunohistochemically with SSEA-1 antibody. The number of PGCs in the left and right gonad in 10 randomly selected sections from each embryo was counted (Table 2). The index of sterility (IS) was calculated (Table 3) using the equation IS=(N−X)/N where N is the PGC number from control gonads and X is the PGC number from busulfan treated embryo (Reynaud, *J. Embryol. Exp.Morphol.* 21:485–507 (1969)).

The effects of treatment with sesame oil. DMF and busulfan on survivability of chick embryos to Stage 27 was determined (Table 4). Hatchability of treated birds following administration of busulfan was also assessed (Table 5).

TABLE 2

Reduction in PGC Number in Stage 27 Chicken Embryos after the Administration of 75 µl Busulfan

| Treatment | Label of Embryo | PGC Number in 10 Random Sections of stage 27 embryos | Average of PGC number |
|---|---|---|---|
| No-injection Control | Noinj7 | 295 | 347 |
| | Noinj8 | 279 | |
| | Noinj9 | 414 | |
| | Noinj10 | 289 | |
| | Noinj11 | 263 | |
| | Noinj12 | 419 | |
| | Noinj14 | 281 | |
| | Noinj15 | 490 | |
| | Noinj16 | 391 | |
| Busulfan Suspension (72 µg Busulfan + 50 µl Sesame Oil) | Buoil1 | 30 | 127 |
| | Buoil3 | 266 | |
| | Buoil4 | 136 | |
| | Buoil5 | 178 | |
| | Buoil6 | 334 | |
| | Buoil7 | 18 | |
| | Buoil8 | 11 | |
| | Buoil9 | 58 | |
| | Buoil10 | 76 | |
| | Buoil11 | 217 | |
| | Buoil12 | 138 | |
| | Buoil15 | 66 | |
| Emulsion Control (25 µl DMF +25 µl Sesame Oil) | J2 | 227 | 275 |
| | M1 | 333 | |
| | M2 | 173 | |
| | M3 | 196 | |
| | J3 | 213 | |
| | J4 | 401 | |
| | J5 | 179 | |
| | J6 | 320 | |
| | J8 | 393 | |
| | M4 | 317 | |
| Busulfan Emulsion (75 µg Busulfan + 25 µl DMF + 25 µl Sesame Oil) | K1 | 7 | 58 |
| | K2 | 64 | |
| | K3 | 96 | |
| | K5 | 75 | |
| | N3 | 43 | |
| | L1 | 91 | |
| | L2 | 82 | |
| | L9 | 8 | |
| | L10 | 86 | |
| | N4 | 54 | |
| | N15 | 36 | |

Statistical Analysis of Table 2 Using STATLETS:

Summary Statistics:

| Sample | Count | Mean | Median | Std. deviation |
|---|---|---|---|---|
| No-injection | 9 | 346.778 | 295.0 | 82.2812 |
| Emulsion | 10 | 275.2 | 272.0 | 87.5351 |
| Bu-suspension | 12 | 127.333 | 106.0 | 103.967 |
| Bu-emulsion | 11 | 58.3636 | 64.0 | 31.69 |

ANOVA Table:

| Source | Sum of Squares | Df | Mean Square | F-Ratio | P-Value |
|---|---|---|---|---|---|
| Between groups | 531444 | 3 | 177148 | 26.71 | 1.0E−4 |
| Within groups | 252066 | 38 | 6633.33 | | |
| Total (corr.) | 783511 | 41 | | | |

Multiple Range Tests:

Method: 95.0 percent LSD

| | Count | Mean | Homogeneous Groups |
|---|---|---|---|
| Bu-emulsion | 11 | 58.3636 | c |
| Bu-suspension | 12 | 127.333 | b |
| Emulsion | 10 | 275.2 | a |
| No-injection | 9 | 346.778 | a |

| Contrast | Difference | +/− Limits |
|---|---|---|
| No-injection − emulsion | 71.5778 | 75.756 |
| No-injection − Bu-suspension | *219.444 | 72.7042 |
| No-injection − Bu-emulsion | *288.414 | 74.107 |
| Emulsion − Bu-suspension | *147.867 | 70.5964 |

-continued

| | | |
|---|---|---|
| Emulsion - Bu-emulsion | *216.836 | 72.0402 |
| Bu-suspension - Bu-emulsion | *68.9697 | 68.8238 |

*denotes a statistically significant difference.
Statistical Interpreter
This table applies a multiple comparison procedure to determine which means are significantly different from which others. The bottom half of the output shows the estimated difference between each pair of means. An asterisk has been placed next to 5 pairs, indicating that these pairs show statistically significant differences at the 95.0% confidence level. At the top of the page, homogenous groups are identified using columns of X's. Within each column, the levels containing X's form a group of means within which there are no statistically significant differences.
The method currently being used to discriminate among the means is Fisher's least significant difference (LSD) procedure. With this method, there is a 5.0% risk of calling each pair of means significantly different when the actual difference equals 0.

TABLE 3

Sterility of Stage 27 Chicken Embryos after the Administration of 75 μl Busulfan Suspension and Busulfan Emulsion

| Treatment | Label of Embryo | Sterility (%) | Average of sterility[1] | Coefficient of Variation |
|---|---|---|---|---|
| Busulfan Suspension (75 μg Busulfan + 50 μl Sesame Oil) | Buoil1 | 91% | 63.25% | 47 |
| | Buoil3 | 23% | | |
| | Buoil4 | 61% | | |
| | Buoil5 | 49% | | |
| | Buoil6 | 4% | | |
| | Buoil7 | 95% | | |
| | Buoil8 | 97% | | |
| | Buoil9 | 83% | | |
| | Buoil10 | 78% | | |
| | Buoil11 | 37% | | |
| | Buoil12 | 60% | | |
| | Buoil15 | 81% | | |
| Busulfan Emulsion (75 μg Busulfan 25 μl DMF + 25 μl Sesame Oil) | K1 | 98% | 83.13% | 11 |
| | K2 | 82% | | |
| | K3 | 72% | | |
| | K5 | 78% | | |
| | N3 | 88% | | |
| | L1 | 74% | | |
| | L2 | 76% | | |
| | L9 | 98% | | |
| | L10 | 75% | | |
| | N4 | 84% | | |
| | N15 | 90% | | |

[1]Note: the average of No-injection control (347 PGCs of ten sections) was used to compute the sterility.

TABLE 4

Effects of Sesame Oil, Dimethyl Formamide (DMF) and Busulfan (Bu) on Survivability of Stage 27 Chicken Embryos

| Treatment | Total Embryos | Embryos survived at stage 27 | Survivability at stage 27 |
|---|---|---|---|
| Oil Control (50 μl Sesame Oil) | 36 | 23 | 63.89% |
| Busulfan Suspension (75 μg Bu + 50 μl Sesame Oil) | 49 | 14 | 28.57%* |
| Emulsion Control (25 μl DMF + 25 μl Sesame Oil) | 32 | 15 | 46.88% |
| Busulfan Emulsion (75 μg Bu + 25 μl DMF + 25 μl Sesame Oil) | 32 | 12 | 37.5% |

*mean survival is significantly different, P < .05.

Statistical Analysis of Table 4 using Chi-square:
There is significant difference between busulfan suspension and oil control ($X^2=9.14$, $p<0.05$). There is no significant difference between busulfan emulsion and emulsion control ($X^2=0.26$, $p>0.05$).

TABLE 5

Effect of Busulfan on the Hatchability of Chicken Embryos

| | Total (fertilized) | Embryos Died early[1] | Embryos Died Late[2] | Chicken Hatched |
|---|---|---|---|---|
| No injection control | 14 | 0 | 1 | 13 (92.86%) |
| Sham injection control | 25 | 0 | 7 | 18 (72%) |
| Emulsion control (25 μl DMF + 25 μl Sesame oil) | 41 | 8 | 10 | 23 (56.10%) |
| Busulfan emulsion (75 μg Bu + 25 μl MF + 25 μl Sesame oil) | 47 | 25 | 8 | 14 (29.79%)* |

[1]Embryos died prior to day 12 of incubation.
[2]Embryos died after day 12 of incubation.
*Significantly different at P < 0.5.

Statistical Analysis of Table 5 Using Chi-square:
There is no significant difference between sham injection and emulsion control ($X^2=1.06$. $P>0.05$). However, there are significant difference between busulfan emulsion and no injection ($X^2=14.93$. $P>0.05$), between busulfan emulsion and sham injection ($X^2=10.13$, $p>0.05$), between busulfan emulsion and emulsion control ($X^2=5019$, $p>0.05$).

EXAMPLE 17

Repopulating Germ Cells in Busulfan Treated Embryos

The busulfan treated birds of EXAMPLE 16 were used as recipients and administered exogenous PGCs from donor birds.
A. Preparation of Donor Cells:
Gonads from 5.5-day chicken embryos were collected in PBS. The isolated gonads were pooled in 250 μl of 0.02% EDTA in a 35 mm petri dish and incubated at 37° C. for 10 min. The gonads were teased with a needle in the petri dish and incubate at 37° C. for 5 more minutes. The cells were collected in DMEM containing 20% FBS and centrifuged at 450 g for 5 min. The cells were washed and resuspended in DMEM. The cells number and viability was determined. The final concentration of viable cells was adjusted to about 1000 cells/μl.
B. Preparation of Busulfan Treated Recipient Embryos:
Recipient chick embryos were prepared and treated with busulfan as described in EXAMPLE 16. The embryos were placed in the incubator until Stage 14–17 (H&H).
C. Injection of Donor PGCs Into Busulfan Treated Recipient Embryos:
Approximately 2 to 3 μl of gonadal cell suspension containing approximately 100 PGCs was injected into the blood vessel of stage 14–17 (H&H) busulfan treated recipient chick embryos. The recipient eggs were sealed and incubated at 37.5° C., 60% relative humidity.
D. Assessment of PGC Repopulation:
The embryos were collected at stage 27 (H&H) and fixed in 4% paraformaldehyde overnight at 4° C. The embryos were embedded in paraffin, sectioned at 7 um thickness and stained immunohistochemically with SSEA-1 antibody. The number of PGCs in the left and right gonad in 10 randomly selected sections from control and PGC injected embryos was counted.

TABLE 6

PGC repopulation after sterilizing the embryos with 75 μg Busulfan

| Treatment | Label of Embryo | PGC number in 10 random sections of stage 27 embryos | Average of PGC number |
|---|---|---|---|
| PGC repopulation (injection of gonadal PGCs 48 hours after busulfan treatment) | ReI1 | 122 | 93.67 |
| | ReI2 | 70 | |
| | ReII1 | 108 | |
| | ReII3 | 40 | |
| | ReII5 | 190 | |
| | ReII6 | 32 | |
| Busulfan Treatment 75 ug Bu + 25 μl DMF + 25 μl Sesame Oil) | Rbu3 | 21 | 22.67 |
| | Rbu4 | 20 | |
| | Rbu8 | 2 | |
| | Rbu10 | 68 | |
| | Rbu11 | 17 | |
| | Rbu12 | 8 | |

Statistical Analysis of Table 6 Using STATLETS:
  Comparison of Population Means for Busulfan control and repopulation:
    Sample sizes=6 and 6
    Means=22.6667 and 93.6667
    Difference of means=−71.0
    95.0% confidence interval for difference of means:
      −71.0+/−57.9184 [−128.918,−13.0816]
    t-test - - -
    Null hypothesis: mu1−mu2=0.0
    Alt. hypothesis: not equal
    Computed t-statistic=−2.7314
    P-value=0.0211426
    Reject the null hypothesis for alpha=0.05
    NOTE: equal standard deviations have been assumed.
Statistical Interpreter
  This table displays the result of a t-test performed to test the null hypothesis that the difference between the means of the populations from which the two samples come equals 0.0 versus the alternative hypothesis that the difference is not equal to 0.0. Since the P-value for this test is less than 0.05, the null hypothesis can be rejected at the 95.0% confidence level. Also shown is a 95.0% confidence interval for the difference between the population means. In repeated sampling, 95.0% of all such intervals will contain the true difference.

EXAMPLE 18

Production of Intra-specific Chicken Germline Chimeras After Depletion of Endogenous PGCs With Busulfan The following procedure may be used to produce intra-specific germline chimeras:
A. Production of Intra-specific Chicken Germline Chimeras:
  Barred Plymouth Rock (BPR) chicken embryos were incubated until stage 27–28 (H&H). Barred Plymouth Rock donor embryos were utilized as a color marker because they are homozygous recessive (ii) at the I locus and express pigment in their plumage. The gonads from male embryos were collected in DMEM, supplemented with 10% FBS, glutamine, antibiotic and antimycotic solution. Sex determination of the embryos was accomplished by utilizing the method of Petitte and Kegelmeyer, (1995) *Animal Biotechnology* 6:19–30. The gonads were then rinsed twice in PBS and incubated in 0.02% EDTA at 37° C. for 15 minutes. Fresh media was added and the gonads were teased apart. The cell suspension was collected and spun at 450×g for 5 minutes. The media was replaced and cell viability determined using trypan blue exclusion. Aliquots of the cell suspension were taken and stained with SSEA-1 antibody to determine the number of PGCs injected. Approximately 2–3 μl of cell suspension, containing 100–500 PGCs, was injected into the blood vessels of White Leghorn (WL) embryos at stages 14–17 (H&H) of development. The WL embryos served as recipients because they were known to be homozygous dominant (II). This genotype codes for an absence of pigment in the plumage. Following the PGC injection, the eggs were returned to the incubator to complete development. At hatching the phenotypic WL chicks were banded and subsequently grown to sexual maturity. The following test matings were conducted to determine if germline chimeras existed: ♂ BPR X ♀WL (BPR PGC) (FIG. 1) and ♂WL (BPR PGC) X ♀ BPR. The offspring from these test matings were subsequently evaluated to determine if ♂BPR gonadal PGC were incorporated in the WL. Since only male BPR embryos were used as donors, all "black" chicks (BPR-phenotype) derived from the ♂ BPR X ♀WL (BPR PGC) test matings would be male.
B. Reducing Endogenous PGC Populations:
  Butsulfan (1,4-butanediol dimethane sulfonate, BU, 15 mg) was dissolved in 5 ml of dimethyl formamide (DMF) in a glass vial and 5 ml of sesame oil (SO) was added. The mixture was vortexed to create an emulsion. The final concentration of BU was 1.5 μg/μl in the emulsion. White Leghorn hatching eggs were incubated at 37.5° C., 60% relative humidity for 22 hours. Then the eggs were placed horizontally in the incubator for 2 hours. The blunt end of each egg cleaned with 70% ethanol. Using a curved forceps, a small hole was then made in the shell covering the air chamber, without damaging the outer shell membrane. Approximately 50 μl of BU emulsion (containing 75 μg) was injected horizontally through the air chamber into the yolk using a hypodermic needle (21G×38.1 mm). The emulsion was vortexed completely before use. The eggs were horizontal for the entire injection procedure. The hole in the shell was sealed with transparent tape and the eggs were incubated vertically after injection. The embryos were collected at stage 27 (H&H) and fixed in 4% paraformaldehyde overnight at 4° C. The embryos were embedded in paraffin, sectioned at 7 μm thickness and stained immunohistochemically with SSEA-1 antibody. The number of PGCs in the left and right gonad in 10 randomly selected sections from each embryo was counted. The index of sterility (IS) was calculated using the equation IS=(N−X)/N where N is the PGC number from control gonads and X is the PGC number from BU-treated embryo (Reynaud, *J. Embryol. Exp.Morphol.* 21:485–507 (1969)).
C. Production of Inter-specific Turkey-hicken Embryonic Germline Chimeras:
  Fertilized turkey eggs were incubated at 38.5° C. for 8–8.5 days (stage 27–28, H&H). Embryos were dissected to obtain gonads. Then 2–3 μl of the gonadal cell suspension, containing approximately 150 PGCs, was injected into the blood vessels stage 14 (H&H) chick embryos. The recipient eggs were sealed and returned to the incubator. Recipient embryos were collected at different stages of incubation (stage 19 to stage 25). The embryos were rinsed in PBS thrice and then fixed in 4% paraformaldehyde overnight at 4° C. Samples were washed three times in PBS and then placed in 50% ethanol. The tissues were then dehydrated, embedded in paraffin, and sectioned. The resulting sections were subsequently analyzed immunohistochemically by staining for SSEA-1 and periodic acid-Schiff (PAS).

D. Results:

Offspring from a WL (II) X BPR (ii) cross would typically express the WL phenotype (Ii) and exhibit an absence of melanin pigment in the plumage. The introduction of male BPR PGC into WL recipients resulted in offspring that demonstrated the black pigment pattern of the BPR. These data support the concept that there are no biological barriers that would prevent the production of increased male offspring by injecting female chick embryos with PGC isolated from the gonads of male embryos. However, the incidence of germline transmission was less than 1%.

The low incidence of donor-derived offspring in this system was possibly related to the significant numerical advantage that endogenous PGC exhibited when compared to the number of injected donor PGC. The treatment of embryos with a BU+DMF+SO emulsion prior to the injection of donor PGC reduced the number of endogenous PGC by as much as 97%. When compared to BU+SO alone, the addition of DMF increased the reduction in endogenous PGC by approximately 15%.

Following the double staining with SSEA-1 and PAS, chick and turkey PGC were identified in the chick embryonic gonad on the basis of differing staining patterns. Due to the presence of glycogen, both chick and turkey PGC stain a magenta color following PAS staining. However, turkey PGC are no longer SSEA-1 positive when they take residence in the developing gonad, distinguishing them from PGC of the chick which are SSEA-1 positive at this stage of development. These results suggest that PGC isolated from the embryonic turkey gonad can be used to repopulate the chick gonad.

Example 19

Production of Intra-specific Chimeras and Test Mating

Using similar protocols to those described in the previous Example, white leghorn (WL) embryos were treated in ovo with a busulfan emulsion (BU+DMF+sesame oil) to deplete endogenous PGCs. Gonads from male Barred Plymouth Rock (BPR) embryos were collected, PGCs isolated, and the isolated PGCs administered to the busulfan emulsion treated birds and control untreated birds in ovo, essentially as described in the preceding example. After hatch, ♂WL (BPR PGC) chimeric birds were raised to sexual maturity and crossed with ♀BPR birds. Production of black offspring is indicative of transmission of the gametes derived from the BPR PGCs by the chimeric ♂WL (BPR PGC) parent.

These studies are ongoing; however the results collected thus far indicate that 25% (4/16) ♂WL (BPR PGC) males are transmitting gametes derived from the BPR PGCs. Among these 4 chimeric birds, the rate of transmission is between about 2% to 23%. In the control birds that were not subjected to busulfan treatment, only one bird had any detectable transmission of the gametes derived from the BPR PGCs.

The foregoing is illustrative of the present invention, and is not to be construed as limiting thereof. The invention is defined by the following claims, with equivalents of the claims to be included therein.

That which is claimed is:

1. A method for the production of avian gametes, comprising:
   reducing the number of primordial germ cells in a recipient avian subject in ovo;
   providing donor primordial germ cells from a donor avian subject;
   introducing the donor primordial germ cells into the recipient avian subject in ovo,
   incubating the recipient avian subject to hatch;
   raising the recipient avian subject to sexual maturity; wherein the recipient avian subject at sexual maturity produces gametes derived from the donor avian subject.

2. The method according to claim 1, wherein the recipient avian subject is from a different avian species than the donor avian subject.

3. The method according to claim 2, wherein the donor avian subject is a whooping crane.

4. The method according to claim 3, wherein the recipient avian subject is a sand hill crane.

5. The method according to claim 1, wherein the donor avian subject is a turkey.

6. The method according to claim 1, wherein the recipient avian subject is a chicken.

7. The method according to claim 1, wherein the recipient avian subject is from the same avian species as the donor avian subject.

8. The method according to claim 1, wherein said step of introducing the donor primordial germ cells is carried out by in ovo injection.

9. The method according to claim 1, wherein the primordial germ cells are gonadal primordial germ cells.

10. The method according to claim 1, wherein the primordial germ cells are blood primordial germ cells.

11. The method according to claim 1, wherein said step of introducing the donor primordial germ cells is carried out by introducing blastodermal cells into the female bird, and wherein the blastodermal cells differentiate into primordial germ cells in the female bird.

12. The method according to claim 1, wherein said step of introducing the donor primordial germ cells is carried out at stage 12 to stage 18 (H&H) of embryonic development of the recipient avian subject.

13. The method according to claim 1, wherein the primordial germ cells carry a pair of male determinative (Z) chromosomes.

14. The method according to claim 1, wherein the primordial germ cells carry a female determinative (w) chromosome.

15. The method according to claim 1, wherein said reducing step comprises administering a composition comprising busulfan to the recipient avian subject in ovo, wherein the composition is administered in an amount effective to reduce the number of primordial germ cells in the recipient avian subject.

16. The method according to claim 15, wherein the busulfan composition is an emulsion.

17. The method according to claim 16, wherein the composition further comprises dimethyl formamide.

18. The method according to claim 15, wherein the busulfan composition comprises from about 50 to about 100 µg busulfan.

19. The method according to claim 15, wherein the composition further comprises a non-toxic oil.

20. The method according to claim 15, where in the step of administering the composition is carried out by in ovo injection.

21. The method according to claim 15, wherein said step of administering the composition is carried out from the time of lay (stage 1; [H&H]) until stage 18 (H&H) of embryonic development of the recipient avian subject.

22. The method according to claim 15, wherein there is a sufficient delay between said step of administering the composition and said step of introducing the donor primordial germ cells so that the amount of busulfan in the recipient avian subject is reduced to less than about 20 µg.

23. The method according to claim 1, wherein the recipient avian subject is a male subject.

24. The method according to claim 1, wherein the recipient avian subject is a female subject.

25. The method according to claim 1, wherein the method further comprises the step of collecting gametes of the donor avian subject from the recipient avian subject.

26. A method of increasing the proportion of male birds in a plurality of bird eggs, comprising:
reducing the number of primordial germ cells in a female bird in ovo;
introducing male (ZZ) avian primordial germ cells into the female bird in ovo;
incubating the female bird to hatch;
raising the female bird to sexual maturity; and
breeding the female bird to produce a plurality of fertile bird eggs;
with the ratio of male to female bird eggs produced from the female bird being greater than that obtained in the absence of administering the male primordial germ cells to the bird in ovo.

27. The method according to claim 26, wherein the primordial germ cells are from the same avian species as the female bird.

28. The method according to claim 26, wherein the female bird is a chicken.

29. The method according to claim 26, wherein the female bird is a turkey.

30. The method according to claim 26, wherein the step of introducing primordial germ cells is carried out by in ovo injection.

31. The method according to claim 26, wherein the primordial germ cells are gonadal primordial germ cells.

32. The method according to claim 26, wherein the primordial germ cells are blood primordial germ cells.

33. The method according to claim 26, wherein said step of introducing the primordial germ cells is carried out at stage 12 to stage 18 (H&H) of recipient embryonic development.

34. The method according to claim 26, further comprising the step of incubating the plurality of fertile bird eggs to hatch;
with the ratio of male to female birds produced from the plurality of fertile bird eggs being greater than that produced in the absence of administering the male primordial germ cells to the female bird in ovo.

35. The method according to claim 26, wherein said introducing step is carried out by injecting the bird with primordial germ cells.

36. The method according to claim 26, wherein said step of introducing the donor primordial germ cells is carried out by introducing blastodermal cells into the female bird, and wherein the blastodermal cells differentiate into primordial germ cells in the female bird.

37. The method according to claim 26, wherein said reducing step comprises administering a composition comprising busulfan to a female bird in ovo, wherein the composition is administered in an amount effective to reduce the number of primordial germ cells in the female bird.

38. The method according to claim 37, wherein the busulfan composition is an emulsion.

39. The method according to claim 38, wherein the composition further comprises dimethyl formamide.

40. The method according to claim 37, wherein the composition administered to the female bird comprises from about 50 to about 100 µg busulfan.

41. The method according to claim 37, wherein the composition further comprises a non-toxic oil.

42. The method according to claim 37, wherein the step of administering the composition is carried out by in ovo injection.

43. The method according to claim 37, wherein said step of administering the composition is carried out from lay (stage 1) until stage 18 (H&H) of embryonic development of the female bird.

44. The method according to claim 37, wherein there is a sufficient delay between said step of administering the composition and said step of introducing the avian primordial germ cells so that the amount of busulfan in the female bird is reduced to less than about 20 µg.

45. A method for the production of avian gametes, comprising:

administering a composition comprising a busulfan emulsion to a recipient chicken subject in ovo, wherein the composition is administered in an amount effective to reduce the number of primordial germ cells in the recipient chicken subject;

providing donor primordial germ cells from a donor avian subject, wherein said donor avian subject is not a chicken;

introducing the donor primordial germ cells into the recipient chicken subject in ovo, incubating the recipient chicken subject to hatch;

raising the recipient chicken subject to sexual maturity; and collecting gametes of the donor avian subject from the recipient chicken subject.

46. A method of increasing the proportion of male chicks in a plurality of chicken eggs, comprising:

administering a composition comprising a busulfan emulsion to a female chicken in ovo, wherein the composition is administered in an amount effective to reduce the number of primordial germ cells in the female chicken;

introducing chicken male (ZZ) primordial germ cells into the female chicken in ovo;

incubating the female chicken to hatch;

raising the female chicken to sexual maturity; and breeding the female chicken to produce a plurality of fertile chicken eggs;

with the ratio of male to female chicken eggs produced from the female chicken being greater than that obtained in the absence of administering the male primordial germ cells to the female chicken in ovo.

* * * * *

UNITED STATES PATENT AND TRADEMARK OFFICE
CERTIFICATE OF CORRECTION

PATENT NO. : 6,691,638 B2
DATED : February 17, 2004
INVENTOR(S) : Pardue et al.

It is certified that error appears in the above-identified patent and that said Letters Patent is hereby corrected as shown below:

Column 21,
Line 35, should read -- (75 µg Busulfan + 25 µl --

Column 27,
Line 7, "met hod" should read -- method --
Line 45, "a bout" should read -- about --

Column 29,
Line 3, "(stage 1)" should read -- (stage 1; [H & H]) --

Signed and Sealed this

First Day of June, 2004

JON W. DUDAS
*Acting Director of the United States Patent and Trademark Office*

SEQUENCE LISTING

<160> NUMBER OF SEQ ID NOS: 2

<210> SEQ ID NO 1
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1
aacagctatg accatg                                                      16

<210> SEQ ID NO 2
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 2
gtaaaacgac ggccagt                                                     17